(12) United States Patent
Molinier et al.

(10) Patent No.: US 9,738,573 B2
(45) Date of Patent: Aug. 22, 2017

(54) APPARATUS FOR THE PRODUCTION OF XYLENES

(71) Applicant: ExxonMobil Chemical Patents Inc., Baytown, TX (US)

(72) Inventors: Michel Molinier, Houston, TX (US); Jeevan S. Abichandani, Houston, TX (US); Jeffrey L. Andrews, Houston, TX (US); Robert G. Tinger, Friendswood, TX (US); Dennis J. Stanley, Houston, TX (US); George J. Wagner, Tomball, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 2 days.

(21) Appl. No.: 15/058,474

(22) Filed: Mar. 2, 2016

(65) Prior Publication Data

US 2016/0185686 A1    Jun. 30, 2016

Related U.S. Application Data

(62) Division of application No. 14/735,753, filed on Jun. 10, 2015, now Pat. No. 9,302,953.
(Continued)

(51) Int. Cl.
*C07C 5/27* (2006.01)
*B01J 19/24* (2006.01)
(Continued)

(52) U.S. Cl.
CPC ............ *C07C 5/277* (2013.01); *B01J 19/24* (2013.01); *B01J 19/245* (2013.01);
(Continued)

(58) Field of Classification Search
CPC .. C07C 5/277; C07C 7/12; C07C 7/04; C07C 6/06; C07C 4/14; C07C 7/005;
(Continued)

(56) References Cited

U.S. PATENT DOCUMENTS 4,886,930 A   12/1989   Zinnen
4,956,522 A    9/1990   Zinnen
(Continued)

FOREIGN PATENT DOCUMENTS

WO   WO 2013/085681   6/2013
WO   WO 2014/058550   4/2014

OTHER PUBLICATIONS

U.S. Appl. No. 62/018,724, filed Jun. 30, 2014, Molinier et al.
U.S. Appl. No. 62/018,726, filed Jun. 30, 2014, Molinier et al.

Primary Examiner — Lessanework Seifu

(57) ABSTRACT

In a process for producing para-xylene, a feed stream comprising $C_{6+}$ aromatic hydrocarbons is separated into a toluene-containing stream, a $C_8$ aromatic hydrocarbon-containing stream and a $C_{9+}$ aromatic hydrocarbon-containing stream. The toluene-containing stream is contacted with a methylating agent to convert toluene to xylenes and produce a methylated effluent stream. Para-xylene is recovered from the $C_8$ aromatic hydrocarbon-containing stream and the methylated effluent stream in a para-xylene recovery section to produce a para-xylene depleted stream, which is then contacted with a xylene isomerization catalyst under liquid phase conditions effective to isomerize xylenes in the para-xylene depleted stream and produce an isomerized stream. The $C_{9+}$-containing stream with a transalkylation catalyst under conditions effective to convert $C_{9+}$-aromatics to $C_{8-}$-aromatics and produce a transalkylated stream, which is recycled together with the isomerized stream to the para-xylene recovery section.

8 Claims, 4 Drawing Sheets

Related U.S. Application Data

(60) Provisional application No. 62/018,726, filed on Jun. 30, 2014.

(51) Int. Cl.

| | | |
|---|---|---|
| *C07C 2/86* | (2006.01) | |
| *C07C 6/12* | (2006.01) | |
| *C07C 6/04* | (2006.01) | |
| *C07C 7/00* | (2006.01) | |
| *C07C 7/13* | (2006.01) | |
| *C07C 7/14* | (2006.01) | |
| *C07C 4/14* | (2006.01) | |
| *C07C 6/06* | (2006.01) | |
| *C07C 7/04* | (2006.01) | |
| *C07C 7/12* | (2006.01) | |
| *C10G 35/04* | (2006.01) | |

(52) U.S. Cl.
CPC ........... *B01J 19/2445* (2013.01); *C07C 2/862* (2013.01); *C07C 2/864* (2013.01); *C07C 4/14* (2013.01); *C07C 5/2729* (2013.01); *C07C 5/2732* (2013.01); *C07C 6/04* (2013.01); *C07C 6/06* (2013.01); *C07C 6/123* (2013.01); *C07C 7/005* (2013.01); *C07C 7/04* (2013.01); *C07C 7/12* (2013.01); *C07C 7/13* (2013.01); *C07C 7/14* (2013.01); *C10G 35/04* (2013.01); *B01J 2219/24* (2013.01)

(58) Field of Classification Search
CPC   C07C 7/13; C07C 7/14; C07C 5/2732; C07C 6/123; C07C 6/04; C07C 5/2729; C07C 2/862; C10G 35/04; B01J 19/2445; B01J 19/24; B01J 19/245; B01J 8/02; B01J 8/04; B01J 8/18; B01J 8/24; B01D 3/14; B01D 3/143

See application file for complete search history.

(56) References Cited

U.S. PATENT DOCUMENTS

| | | |
|---|---|---|
| 5,057,643 A | 10/1991 | Zinnen |
| 5,516,956 A | 5/1996 | Abichandani et al. |
| 5,563,310 A | 10/1996 | Chang et al. |
| 5,625,103 A | 4/1997 | Abichandani et al. |
| 6,423,879 B1 | 7/2002 | Brown et al. |
| 6,504,072 B1 | 1/2003 | Brown et al. |
| 6,642,426 B1 | 11/2003 | Johnson et al. |
| 7,663,010 B2 | 2/2010 | Levin |
| 7,989,672 B2 | 8/2011 | Kinn et al. |
| 9,012,711 B2 | 4/2015 | Ou et al. |
| 2010/0228066 A1 | 9/2010 | Kong et al. |
| 2011/0009682 A1 | 1/2011 | Matsushita et al. |
| 2011/0263918 A1 | 10/2011 | Ou et al. |
| 2011/0319688 A1 | 12/2011 | Ou |
| 2012/0149958 A1* | 6/2012 | Ellrich .................. C07C 2/864 585/321 |
| 2012/0316375 A1 | 12/2012 | Zheng et al. |
| 2013/0296624 A1 | 11/2013 | Iaccino et al. |
| 2014/0100402 A1 | 4/2014 | Gawlik et al. |

\* cited by examiner

US 9,738,573 B2

APPARATUS FOR THE PRODUCTION OF XYLENES

CROSS REFERENCE TO RELATED APPLICATIONS

The present application is a divisional of and claims priority to and the benefit of U.S. patent application Ser. No. 14/735,753, filed Jun. 10, 2015, and U.S. Provisional Application No. 62/018,726, filed Jun. 30, 2014, which is incorporated by reference in its entirety. Related applications are U.S. Provisional Application No. 62/018,724, filed Jun. 30, 2014, U.S. Non-Provisional application Ser. No. 14/735,695, filed Jun. 10, 2015 and U.S. Non-Provisional application Ser. No. 14/735,531, filed Jun. 10, 2015.

FIELD OF THE INVENTION

This invention relates to a process for the production of xylenes and particularly for the production of para-xylene.

BACKGROUND OF THE INVENTION

A major source of xylenes is catalytic reformate, which is produced by contacting petroleum naphtha with a hydrogenation/dehydrogenation catalyst on a support. The resulting reformate is a complex mixture of paraffins and $C_6$ to $C_8$ aromatics, in addition to a significant quantity of heavier aromatic hydrocarbons. After removing the light ($C_5$-) paraffinic components, the remainder of reformate is normally separated into $C_{7-}$, $C_8$, and $C_{9+}$-containing fractions using a plurality of distillation steps. Benzene can then be recovered from the $C_{7-}$-containing fraction to leave a toluene-rich fraction which is generally used to produce additional $C_8$ aromatics by toluene disproportionation and/or transalkylation with part of the $C_{9+}$-aromatics containing fraction. The $C_8$-containing fraction is fed to a xylene production loop where para-xylene is recovered, generally by adsorption or crystallization, and the resultant para-xylene depleted stream is subjected to catalytic conversion to isomerize the xylenes back towards equilibrium distribution. The resultant isomerized xylene stream can then be recycled to the para-xylene recovery unit.

Although benzene and toluene are important aromatic hydrocarbons, the demand for xylenes, particularly para-xylene, outstrips that for benzene and toluene and currently is growing at an annual rate of 5-7%. There is therefore a continuing need to develop aromatics production technologies which maximize the production of para-xylene, while minimizing the associated capital and operating costs.

SUMMARY OF THE INVENTION

According to the present invention, an improved method of producing para-xylene, optionally together with benzene and/or ortho-xylene, has now been developed in which a methylation unit is added to a para-xylene production complex to convert toluene and/or benzene in a reformate or similar aromatics fraction to additional xylenes. The methylation unit produces a $C_8$ aromatic product rich in para-xylene but with little or no additional ethylbenzene. As a result, the production and operating costs of the xylenes separation section can be reduced and less costly liquid phase processes can be used for at least part of the xylene isomerization section. If needed, build-up of ethylbenzene in the xylene production loop can be avoided by addition of a vapor phase isomerization unit and/or by feeding part of the para-xylene depleted stream to the transalkylation unit, and/or by separating the ethylbenzene from the xylenes stream using conventional technology such as distillation, or membranes, or selective adsorption, or combinations thereof.

Thus, in one aspect, the invention resides in a process for producing para-xylene, in which a feed stream comprising $C_{6+}$ aromatic hydrocarbons is separated into at least a toluene-containing stream, a $C_8$ aromatic hydrocarbon-containing stream and a $C_{9+}$ aromatic hydrocarbon-containing stream. At least part of the toluene-containing stream is contacted with a methylating agent under conditions effective to convert toluene to xylenes and produce a methylated effluent stream. Para-xylene is recovered from the C8 aromatic hydrocarbon-containing stream and the methylated effluent stream to produce at least one para-xylene depleted stream. At least part of the para-xylene depleted stream is contacted with a xylene isomerization catalyst under liquid phase conditions effective to isomerize xylenes in the para-xylene depleted stream and produce an isomerized stream, which is recycled to the para-xylene recovery step. At least part of the $C_{9+}$-containing stream is contacted with a transalkylation catalyst under conditions effective to convert $C_{9+}$-aromatics to $C_{8-}$-aromatics and produce a transalkylated stream, which is recycled to one or more of the toluene methylation step and para-xylene recovery step.

In a further aspect, the invention resides in apparatus for producing para-xylene comprising a catalytic reformer for producing a reformate stream comprising $C_{6+}$ aromatic hydrocarbons; a first separation system for separating the reformate stream into at least a toluene-containing stream, a $C_8$ aromatic hydrocarbon-containing stream and a $C_{9+}$ aromatic hydrocarbon-containing stream; a toluene methylation unit for converting toluene in the toluene-containing stream to xylenes and produce a methylated effluent stream; a second separation system for recovering para-xylene from the $C_8$ aromatic hydrocarbon-containing stream, the methylated effluent stream and a transalkylation effluent stream to produce at least one para-xylene depleted stream; a liquid phase xylene isomerization unit for isomerizing xylenes in the at least one para-xylene depleted stream to produce a first isomerized stream; a recycle system for recycling at least part of the first isomerized stream to the second separation system; and a transalkylation unit for converting $C_{9+}$ aromatics in the $C_{9+}$ aromatic hydrocarbon-containing stream to $C_{8-}$ aromatics and produce the transalkylation effluent stream.

DETAILED DESCRIPTION OF THE EMBODIMENTS

Figure 1:
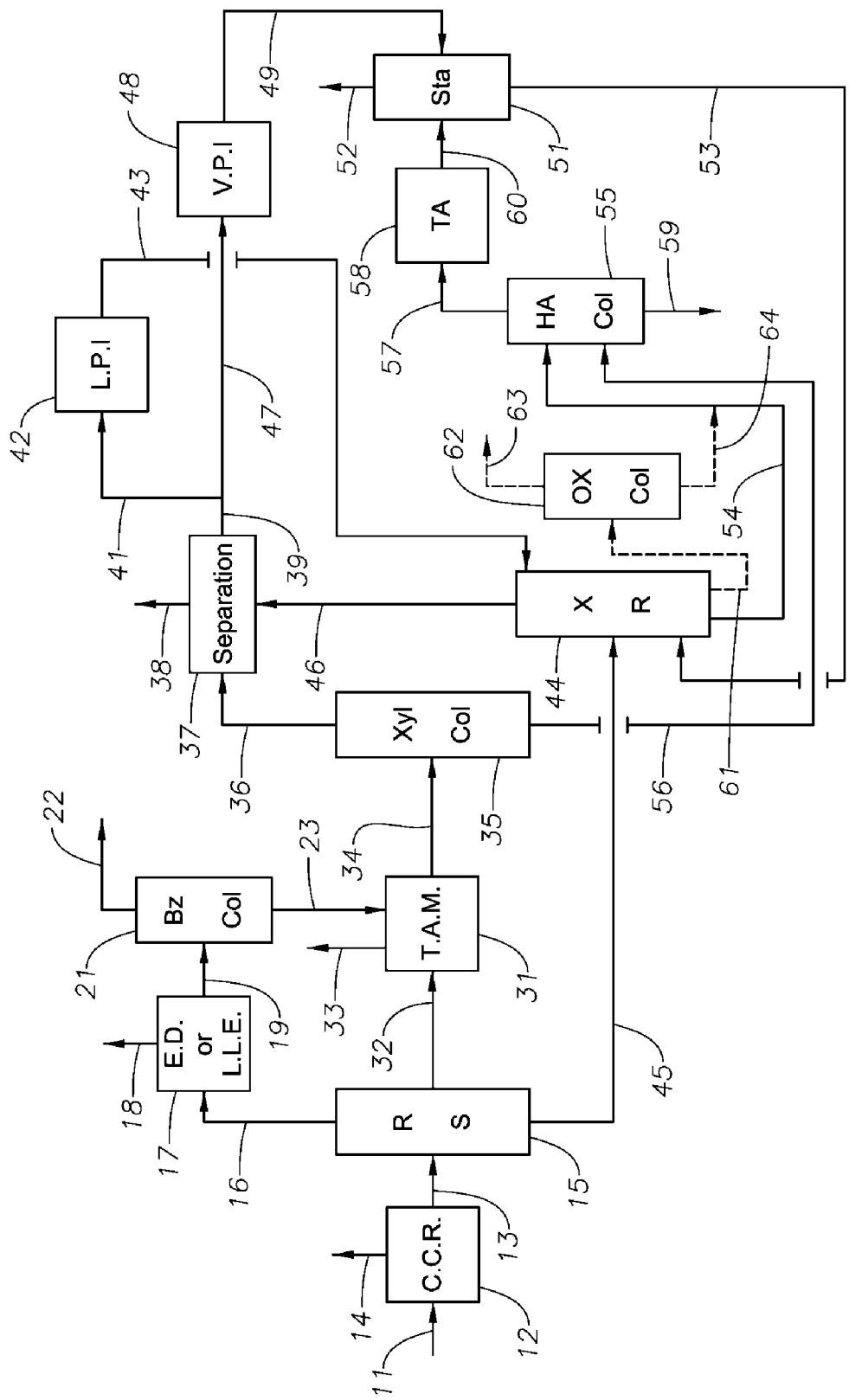
FIG. 1 is a flow diagram of a process for producing para-xylene from catalytic reformate according to a first embodiment of the invention.

The present invention describes a method and apparatus for producing para-xylene, optionally together with benzene and/or ortho-xylene, from a reformate or similar aromatics fraction. In the present process, a methylation unit is added to a para-xylene production complex to convert toluene and/or benzene in the reformate fraction to additional xylenes. Since the methylation unit can produce a $C_8$ aromatic product rich in para-xylene with little or no additional ethylbenzene, the production and operating costs of the xylenes separation section can be reduced and less costly liquid phase processes can be used in the xylene isomerization section. If needed, build-up of ethylbenzene in the xylene production loop can be avoided by addition of a vapor phase isomerization unit and/or by feeding part of the para-xylene depleted stream to the transalkylation unit, and/or by separating the ethylbenzene from the xylenes stream using conventional technology such as distillation, or membranes, or selective adsorption, or combinations thereof.

Any method known in the art for adding methyl groups to a phenyl ring can be used in the methylation step of the present process. However, in certain preferred embodiments, the methylation step employs a highly para-selective methylation catalyst, such as that employed in U.S. Pat. Nos. 6,423,879 and 6,504,072, the entire contents of which are incorporated herein by reference. Such a catalyst comprises a molecular sieve having a Diffusion Parameter for 2,2-dimethylbutane of about 0.1-15 $sec^{-1}$, such as 0.5-10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient ($cm^2/sec$) and r is the crystal radius (cm). The required diffusion parameters can be derived from sorption measurements provided the assumption is made that the plane sheet model describes the diffusion process. Thus, for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967, the entire contents of which are incorporated herein by reference.

The molecular sieve employed in the para-selective methylation process is normally a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene, and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are particularly effective for the present methylation process since the size and shape of their pores favor the production of p-xylene over the other xylene isomers. Conventional forms of these zeolites have Diffusion Parameter values in excess of the 0.1-15 $sec^{-1}$ range referred to above. However, the required diffusivity for the catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, such as at least one oxide selected from elements of Groups 2 to 4 and 13 to 16 of the Periodic Table. Most preferably, said at least one oxide modifier is selected from oxides of boron, magnesium, calcium, lanthanum, and most preferably phosphorus. In some cases, the zeolite may be combined with more than one oxide modifier, for example a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier into the catalyst is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Suitable phosphorus compounds include, but are not limited to, phosphonic, phosphinous, phosphorous and phosphoric acids, salts and esters of such acids and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours. Similar techniques known in the art can be used to incorporate other modifying oxides into the catalyst employed in the alkylation process.

In addition to the zeolite and modifying oxide, the catalyst employed in the methylation process may include one or more binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite. Preferably, the matrix material comprises silica or a kaolin clay.

The methylation catalyst used in the present process may optionally be precoked. The precoking step may be carried out by initially loading uncoked catalyst into the methylation reactor. Then, as the reaction proceeds, coke is deposited on the catalyst surface and thereafter may be controlled within a desired range, typically from about 1 to about 20 wt % and preferably from about 1 to about 5 wt %, by periodic regeneration through exposure to an oxygen-containing atmosphere at an elevated temperature.

Methylation of toluene in accordance with the present process can be effected with any known methylating agent, but preferred methylating agents include methanol and/or a mixture of carbon monoxide and hydrogen.

Suitable conditions for the methylation reaction include a temperature from 350 to 700° C., such as from 500 to 600° C., a pressure of from 100 and 7000 kPa absolute, a weight hourly space velocity of from 0.5 to 1000 hr$^{-1}$, and a molar ratio of toluene to methanol (in the reactor charge) of at least about 0.2, e.g., from about 0.2 to about 20. The process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in a catalyst regenerator. One example of a suitable fluidized bed process for methylating toluene includes staged injection of the methylating agent at one or more locations downstream of the toluene feed location. Such a process in described in U.S. Pat. No. 6,642,426, the entire contents of which are incorporated herein by reference.

Using the present process, toluene can be alkylated with methanol so as to produce para-xylene at a selectivity of at least about 75 wt % (based on total $C_8$ aromatic product) at a per-pass aromatic conversion of at least about 15 wt % and a trimethylbenzene production level less than 1 wt %. Unreacted toluene and methylating agent and a portion of the water by-product may be recycled to the methylation reactor and heavy byproducts routed to fuels dispositions. The $C_8$ fraction is routed to a para-xylene separation section, which typically operates by fractional crystallization or by selective adsorption or both to recover a para-xylene product stream from the alkylation effluent and leave a para-xylene-depleted stream containing mainly $C_7$ and $C_8$ hydrocarbons. Since the toluene methylation unit enhances the para-xylene content of the reformate $C_8$ fraction, the size of the para-xylene separation section can be reduced. This is a significant advantage since the para-xylene separation section is one of the most expensive processes in an aromatics complex both from a capital cost and from an operating expense perspective.

After recovery of para-xylene in the para-xylene separation section, the remaining para-xylene-depleted stream is isomerized back to equilibrium before being recycled back to the para-xylene separation section. In the present process, isomerization of the para-xylene-depleted stream is conducted in a liquid phase isomerization unit, either alone or connected in parallel with a vapor phase isomerization unit, such that the units operate simultaneously or alternately.

Any liquid phase catalytic isomerization process known to those skilled in the art can be used in the liquid phase xylene isomerization unit, but one preferred catalytic system is described in U.S. Patent Application Publication Nos. 2011/0263918 and 2011/0319688, the entire contents of each of which are incorporated herein by reference. Suitable conditions for the liquid phase isomerization process used herein include a temperature from about 230° C. to about 300° C. and a pressure from about 1300 to about 3500 kPa selected to maintain the para-xylene-depleted stream substantially in the liquid phase. In some embodiments, the weight hourly space velocity (WHSV) may be from about 0.5 to about 10 hr$^{-1}$.

Where present, the vapor phase isomerization unit can also employ any known isomerization catalyst system, but preferably employs a catalyst system effective to convert some or all of the ethylbenzene in the para-xylene-depleted stream as well as to return the xylenes to equilibrium concentration. Ethylbenzene removal can be effected either by dealkylation to benzene or by isomerization to xylenes. One preferred vapor phase isomerization process is described in U.S. Pat. No. 5,516,956, the entire contents of which are incorporated herein by reference. Suitable conditions for the vapor phase isomerization process include a temperature of from about 660° F. to about 900° F. (350° C. to 480° C.), a pressure from about 50 to about 400 psig (446 to 2860 kPa), a WHSV of between about 3 and about 50 hr$^{-1}$ and a hydrogen to hydrocarbon molar ratio from about 0.7 to about 5.

The present process also employs a transalkylation unit to convert $C_9$ aromatics, $C_{10}$ aromatics and some $C_{11}$ aromatics in the reformate feed to equilibrium xylenes either directly or by reaction with benzene or toluene routed from other parts of the process. The xylenes in the transalkylation effluent can then be fed to the para-xylene separation section for recovery of para-xylene, while any benzene or toluene produced in the transalkylation process is conveniently supplied to the toluene methylation unit for further upgrading to additional xylenes. Any liquid phase or vapor phase transalkylation unit can be used in present process, but one preferred unit employs the multi-stage catalytic system described in U.S. Pat. No. 7,663,010, the entire contents of which are incorporated herein by reference. The transalkylation unit can be used to generate benzene and toluene using xylenes and $C_{9+}$ aromatic feeds as described in U.S. Patent Application Publication No. 2012/0149958, the entire contents of which are incorporated herein by reference, of which the benzene and/or toluene can be used as feed to the toluene methylation unit to produce higher para-xylene purity feeds to the para-xylene recovery stages. Additionally, some of or all off site benzene, or import benzene feeds, can be transalkylated with $C_{9+}$ aromatic feeds to generate toluene and/or xylenes. Finally, the $C_{9+}$ aromatic molecules can be fractionated into a concentrated $C_9$ stream consisting of propylbenzenes and methylethylbenzenes which is transalkylated with benzene to produce toluene and ethylbenzenes. The toluene and ethylbenzene can then be processed in the toluene methylation unit to generate paraxylene and light olefins for recovery. In addition to the toluene produced by the reforming section and/or the transalkylation section, imported toluene can also be fed to the toluene methylation unit for incremental paraxylene production. Such imported toluene is preferably oxygen stripped and tanks for storage of such imported toluene are preferably nitrogen blanketed. The invention will now be more particularly described with reference to the accompanying drawings.

FIG. 1 illustrates a process for producing para-xylene according to a first embodiment of the invention, in which a naphtha feedstock is supplied by line 11 to a catalytic reformer (for example, a semi-regenerative reformer, a cycle reformer or a continuous catalytic reformer) 12. The effluent from the catalytic reformer 12 is a complex mixture of aliphatic and aromatic hydrocarbons and, after removal of the $C_{5-}$ fraction in a depentanizer (not shown), the remaining $C_{6+}$ fraction is fed by line 13 to a reformate splitter 15. Hydrogen is also generated in the catalytic reformer 12 and is removed via line 14 for use in the gas phase isomerization section described below, or in various units in a refinery, or in a cyclohexane unit or any other petrochemical process if the aromatics complex is not erected next to a refinery. Alternatively, the hydrogen can be sold as export, or used in fuel, or flared.

The reformate splitter 15, which can optionally be a dividing-wall distillation column, separates the $C_{6+}$ fraction in line 13, in one embodiment, into a $C_{6-}$-containing overhead stream, a $C_7$-containing intermediate stream and a $C_{8+}$-containing bottoms stream. The $C_{6-}$-containing overhead stream may also contain some or all of the toluene and/or $C_8$ aromatics present in line 13 along with their non-aromatic co-boilers, depending on specific economic objectives. In another embodiment (not shown), the reformate splitter 15 separates the $C_{6+}$ fraction in line 13 into a $C_{7-}$-containing overhead stream and a $C_{8+}$-containing bottoms stream, omitting the recovery of an intermediate stream. Again, the $C_{7-}$-containing overhead stream may also contain some or all of the $C_8$ aromatics present in line 13 along with their non-aromatic co-boilers, depending on specific economic objectives.

Returning to FIG. 1, the $C_{6-}$-containing overhead stream, or the $C_{7-}$-containing overhead stream in the alternate embodiment, from the reformate splitter 15 is sent via line 16 to an extraction section 17, which can be a liquid-liquid extraction process, an extractive distillation type process or a hybrid thereof. Non-aromatics raffinate is removed from the extraction section 17 via line 18 and can be used in an olefins oligomerization or reformate alkylation unit, or as feed to a steam cracker or to the refinery gasoline pool, or as fuel. The raffinate can also be used as feed to an aromatization unit to produce additional aromatic molecules while generating hydrogen. The aromatics product from extraction section 17 is removed via line 19 and is supplied to a benzene column 21, optionally after pretreatment with clay or a molecular sieve catalyst to remove trace olefins or other low level impurities. Entrained water is removed from the aromatics extraction product in benzene column 21 and a benzene product is collected via line 22, typically as a sidestream from the benzene column 21. The benzene column bottoms product is rich in toluene, although it may also contain some trace xylenes and heavier alkylaromatics, and is sent via line 23 to a toluene methylation section 31. The benzene in line 22 can either be recovered for sale or hydrogenation to produce cyclohexane or can be fed to the toluene methylation section 31 for additional xylenes production.

The toluene methylation section 31 also receives the $C_7$-containing intermediate stream from the reformate splitter 15 via line 32 together with a supply of methylating agent, typically methanol (not shown in FIG. 1) or dimethyl ether. It should be noted that the split between line 16 ($C_{6-}$-containing overhead stream from the reformate splitter 15) and line 32 ($C_7$-containing intermediate stream from the reformate splitter 15) can be used to effectively control the level of non-aromatics sent to the toluene methylation section 31 since non-aromatics exiting reformate splitter 15 via line 16 to the extraction section 17 will be removed via line 18. Hence additional flow through line 16 will reduce overall non-aromatics content in the feed to the toluene methylation section 31.

In the toluene methylation section 31, toluene from lines 23 and 32, optionally together with benzene from column 21, is reacted with methanol to produce xylenes and water. In some instances, $C_8$ aromatics are also fed to the toluene methylation section 31 via lines 23 and 32, to carry out ethylbenzene dealkylation to benzene in the toluene methylation section 31, with possible subsequent benzene methylation to toluene or xylenes in said section 31.

The toluene may be routed through a toluene furnace and/or heat exchange equipment (not shown) prior to entering the toluene methylation section 31 to vaporize the toluene and heat it to the temperature required to maintain the methylation reaction, which is dependent on the type of catalyst(s) used for the methylation process. Some catalysts require the toluene to be preheated to 400° C. while other catalysts require the toluene to be preheated to 600° C. The toluene can be heated to these temperatures in process heat exchanger equipment and/or furnaces, depending on the available heat sink in the process. Toluene that is heated to high temperatures, for example in a furnace, may reach temperatures that decompose the toluene to coke or heavier hydrocarbons which can impact the heat transfer rate. This decomposition rate can be reduced by co-feeding a diluent with the toluene upstream of the heat transfer equipment, such as nitrogen, hydrogen, fuel gas, steam, or a combination thereof. The molar ratio of these diluents to toluene can vary from 0.01 to greater than 10. Toluene decomposition can also be managed using the proper metallurgy for tubes, either in the convection section or radiant section, as one skilled in the art will understand. Examples include carbon steel, stainless steels, titanium, or other alloys. Special coatings and applications may also be used to minimize toluene decomposition effects and minimize coking. Additionally, additives may be used to minimize toluene coking.

The efficiency of the methylation reaction improves as the methylating agent, typically methanol, is broadly and widely distributed within the reactor. The methylating agent can be introduced into the fixed bed or fluid bed reactor in a number of different ways, such as via a single injection point, several injection points, or even via a sparger arrangement. The methylating agent can be dispersed into the reactor either through nozzles that are flush to the reactor vessel or through an internal distribution network. The number of nozzles flush to the reactor can be one, a few or many. Alternatively, the methylating agent can be introduced into the fixed bed or fluid bed through an internal distributor. The internal distributor may be a single injection point, a few injection points or many injection points. In the case of a few or many injection points, the distributor may contain arteries branching off of one or more common headers, and additional sub-arteries may branch off of each artery to form a network of arteries. The arteries may be designed to have a uniform diameter, either the same or different diameter as the common headers, or be tapered in various diameters and different lengths. Along each common header or artery there may be one or several or many nozzles to introduce the methylating agent. The size and length of these nozzles may be similar or different depending on the required distribution of the methylating agent into the reactor. The internal distributor, arteries, and nozzles may be insulated if used in a fluid bed or fixed bed reactor. The decision to insulate or not can change the metallurgical requirements, which can range from carbon steel or to stainless steels or to titanium or other types of alloys commonly used. The bulk temperature of the methylating fluid and the skin temperatures inside of the distribution network are preferred to be below the decomposition temperature of the methylating agent, which is known to one skilled in the art. The decomposition rate of the methylating agent can be reduced by co-feeding a diluent, such as nitrogen, hydrogen, fuel gas, steam, or a combination thereof. The molar ratio of these diluents to methylating agent can vary from 0.01 to greater than 10. The ideal distribution system for a methylating agent is a fractal distributor which contains an order of magnitude number of arteries and nozzles located both radially and axially throughout the reaction zone. The fractal distribution system can be designed to introduce the methylating agent at the same or different rate axially inside the reactor. The axial distribution can also be controlled having two or more fractal distributors with rates of methylating agent controlled externally from the reactor via common engineering methods, i.e., valves, pumps, restriction orifices, etc.

The process off-gas from the toluene methylation section 31 is collected by line 33 and can be used in an olefins oligomerization unit or a reformate alkylation unit, or can be sent to a steam cracker or refinery for olefins recovery, or used as fuel gas. The remainder of the product from the toluene methylation section 31 is fed via line 34 to a xylene distillation column 35, which divides the methylation product into a para-xylene rich $C_8$ aromatics overhead stream and a $C_{9+}$ bottoms stream. Because the quantity of the $C_9$ aromatics is small, the residence time of the $C_9$ aromatics in the distillation column bottoms circuit, i.e., reboiler circuit, can be very high. These $C_9$ aromatics can then polymerize or condense into higher hydrocarbon components when exposed to high temperature and a long period, which may foul the bottoms circuit or heat exchange equipment. Additives can be used to control the rate of heavy polymerization or condensation. Alternatively another source of $C_9$ aromatics can be added to the distillation column to dilute the $C_9$ aromatics from the toluene methylation process. This additional source of $C_9$ aromatics can be introduced either continuously or in batch mode or in semi-batch mode, and purged from the system along with the toluene methylation $C_9$ aromatics, either continuously or batch or semi-batch mode. The additional source of $C_9$ aromatics can be introduced into the distillation column at any location in the distillation column as one skilled in the art will be able to determine.

Prior to the xylene distillation tower 35, the product stream from the toluene methylation section 31 may be fed through a toluene distillation tower (not shown) to recover uncoverted toluene from the xylenes and heavier components. Fresh toluene may also be fed through the toluene distillation tower. The feed point to the toluene distillation tower for product stream and fresh toluene may be the same or different as one skilled in the art will be able to determine. Additionally, there may be other streams that can be fed to the toluene distillation tower, for example a xylenes and heavier stream from a naphtha reformer, xylene isomerization unit, disproportionation unit, transalkylation unit, or any other unit that may contain toluene and heavier aromatics. The toluene from the toluene distillation unit is typically recovered as a liquid overhead product, after condensing via conventional cooling methods such as an air fin, water cooler or process cooler, or combination thereof, either in parallel or series configuration. The toluene may also be recovered as a vapor product, either in the overhead of the distillation tower, upstream of any cooling equipment, or as a side stream from the distillation column. Likewise, the toluene can be recovered as a liquid product from one of the trays in the distillation tower, for example, 3-5 trays below the overhead of the distillation tower. This is particularly effective if the distillation tower contains a component or components lighter than toluene, for example, water or light hydrocarbons, which could reduce the concentration of toluene by dilution. The distillation column to separate toluene from heavier aromatics and impurities may also be a divided wall column, with one or more than one partitions. The recovered toluene may then be recycled back to the toluene methylation section 31 and the heavier components sent downstream for further processing.

The para-xylene rich $C_8$ aromatics overhead stream from the xylene distillation column 35 is sent via line 36 to a separation section 37, where para-xylene product is recovered via line 38. The separation section 37 can be based on an adsorption process or a crystallization process or any combination of both, but in any case it can be optimized to manage para-xylene separation from three separate streams, namely one with ~20% para-xylene content ($C_8$ portion of the reformate), one with preferably ≥75% para-xylene content (toluene methylation process effluent), and one with equilibrium (~24%) para-xylene content (transalkylation and/or isomerization effluent). Such optimization will result in substantial downsizing of the overall separation section 37 as well as considerable savings in utilities consumption. Such optimization may include feeding the para-enriched xylenes stream independent of equilibrium xylenes stream as described in U.S. Pat. Nos. 8,168,845; 8,529,757; 8,481,798; 8,569,564; 8,580,120; U.S. Patent Application Publication No. 2012/0241384; and U.S. Provisional Patent Application No. 61/946,052, the entire contents of which are incorporated herein by reference. Alternatively, a para-xylene enriched product or intermediate product from the adsorption process, which has a para-xylene purity less than 99.7 wt %, can be fed to the crystallization unit to enrich the para-xylene to higher concentrations. Likewise, the crystallization product or intermediate product having a para-xylene purity less than 99.7 wt % may be fed to the adsorption process to enrich the para-xylene to higher concentrations.

Invariably there will be a small amount of toluene present in the xylenes feed to the para-xylene separation section 37. If a Simulated Moving Bed (SMB) Adsorption unit is used to recover para-xylene, a fraction of the toluene present in the xylenes feed will be fractionated as a "crude" toluene product, which may contain trace amounts of xylenes or water. This stream can be sent directly to the toluene methylation section 31 without any treatment to remove trace xylenes or water, since the feed to the toluene methylation section 31 generally contains water co-feed to improve methanol utilization and to suppress feed preheat coking. A combination of both an adsorption process and a crystallization process in separation section 37 may include a small SMB unit (not shown) and a small crystallization unit (not shown) operating in series or in parallel, with the SMB unit primarily dedicated to para-xylene separation from equilibrium xylenes streams and the crystallization unit primarily dedicated to para-xylene separation from the para-xylene enriched stream.

After recovery of the para-xylene, the remaining liquid phase para-xylene depleted effluent from the separation section 37 is collected via line 39 and can be fed in the liquid phase via line 41 to a liquid phase xylenes isomerization section 42 where xylenes are isomerized to equilibrium. The effluent from the liquid phase isomerization section 42 contains close to equilibrium para-xylene (~24%) and is supplied by line 43 to a xylene rerun column 44, which also receives the $C_{8+}$-containing bottoms stream from the reformate splitter 15 via line 45. A $C_8$-rich overhead stream is removed as overhead from the xylene rerun column 44 and is fed via line 46 to separation section 37 where para-xylene product is collected via line 38.

In some embodiments (not shown), the effluent from the liquid phase isomerization section 42 can be sent directly to separation section 37 (without separation in the xylene rerun column 44) provided the concentration of heavy aromatics produced across the liquid phase isomerization section 42 is within the specification of the separation process used in separation section 37. U.S. Pat. No. 7,989,672, the entire contents of which are incorporated herein by reference, teaches the maximum allowable $C_{9+}$ aromatics concentration for a crystallization unit, which can also apply within limits to a simulated moving bed adsorption process, or hybrids of a crystallization and a simulated moving bed adsorption process. In the case of feeding directly from a liquid phase isomerization unit to a simulated moving bed adsorption unit, the $C_9$ aromatics processed across the adsorption unit can be removed from the desorbent fluid by taking all of or a slip stream of the desorbent and processing across a fractionation tower designed to remove $C_9$ aromatics in the desorbent, either as a heavy component, i.e., having a boiling point heavier than the desorbent, or as a light component, i.e., having a boiling point lighter than the desorbent. Desorbent examples include toluene, paradiethylbenzene, or tetralin. Other possible desorbents may also be used depending on the relative selectivity to paraxylene and adsorption raffinate, i.e., metaxylene, orthoxylene, and ethyl benzene. U.S. Pat. No. 8,697,929, the entire contents of which are incorporated herein by reference, teaches that $C_9$ aromatics formation can be reduced if dissolved hydrogen is co-fed to the liquid isomerization unit, thereby reducing the amount of heavy purging required within the simulated moving bed adsorption process. In this case, the $C_9$ aromatics formation may be low enough to provide adequate separation from the xylenes fraction by introducing the liquid phase isomerate to the top tray of xylene rerun column 44 or xylene column 35. Any dissolved hydrogen present can be vented from the system by one skilled in the art of fractionation design.

$C_9$ aromatics formation across the liquid phase isomerization catalysts are also a function of the amount of ethylbenzene present in the feed. The absence of EB or a reduction of EB in the feed to the liquid isomerization unit will reduce the $C_9$ aromatics formation such that fractionation of $C_9$ aromatics is not necessary prior to the adsorption unit. EB can be removed from the liquid phase isomerization unit feed using membranes or adsorption technologies selective for EB.

Alternatively, the para-xylene depleted effluent of separation section 37 collected via line 39 can be fed in the gas phase via line 47 to a vapor phase xylenes isomerization section 48 where xylenes are isomerized to equilibrium. The effluent from vapor phase isomerization section 48 contains close to equilibrium paraxylene (~24%) and is fed by line 49 to stabilizer column 51, where a $C_7$-containing overhead stream is removed via line 52 and the $C_{8+}$ bottoms stream is collected and fed by line 53 to the xylene rerun column 44. When the vapor phase isomerization process used in isomerization section 48 is an ethylbenzene dealkylation type, the overhead stream in line 52 contains dealkylation product benzene and some by-product toluene. When the vapor phase isomerization process used in isomerization section 48 is an ethylbenzene isomerization type, the overhead stream in line 52 contains little benzene and toluene by-products. In either case, benzene can be fed to the extraction section 17 and sold as a product or sent to a cyclohexane unit. Benzene can also be processed in the toluene methylation section 31 or in a transalkylation section (as described below) for additional xylenes production (see other aromatics complex schemes depicted below). Toluene effluent from isomerization section 48 will be processed in the toluene methylation section 32 or in the transalkylation section for additional xylenes production. The combined vapor phase benzene/toluene stream in line 52 can be sent directly to the toluene methylation unit, thereby reducing fractionation costs and maximizing capital utilization.

The $C_{8+}$ bottoms stream removed from the stabilizer column 51 via line 53 is fed to the xylene rerun column 44 along with the $C_{8+}$-containing bottoms stream 45 from the reformate splitter 15 and optionally, the effluent from the liquid phase isomerization section 42. The xylene rerun column 44 separates $C_{9+}$ aromatics from these streams and supplies the $C_{9+}$ aromatics via line 54 to a heavy aromatics column 55, which also receives the $C_{9+}$ bottoms stream from the xylene column 35 via line 56. The heavy aromatics column 55 removes $C_9$ aromatics, $C_{10}$ aromatics and some $C_{ii}$ aromatics from the streams 54 and 56 and feeds these components via line 57 to a transalkylation section 58, while heavier compounds in the streams 54 and 56 are collected via line 59 for supply to the fuel oil pool and/or to another hydrocarbon processing unit which may be able to upgrade the heavier compounds to a more desirable, valuable product or products.

In the transalkylation section 58, $C_9$ aromatics, $C_{10}$ aromatics and some $C_{11}$ aromatics are converted to equilibrium xylenes either directly or by reaction with benzene or toluene routed from other parts of the process. While there are many options to optimize para-xylene production in an aromatics complex operating a toluene methylation unit (such as toluene methylation section 31) and a transalkylation unit (such as transalkylation section 58), since toluene methylation is highly selective to paraxylene, and transalkylation produces a mixed xylenes product, in a preferred embodiment, all toluene introduced or produced in the aromatics complex is sent to the toluene methylation section 31 rather than the transalkylation section 58. Toluene sources in the complex, illustrated in FIG. 1, include toluene from the reformate splitter 15 in optional line 32, toluene from the benzene column 21 in line 23, unconverted toluene in the effluent from the toluene methylation section, "crude" toluene from the para-xylene separation section 37, by-product toluene from the vapor phase isomerization section 48 when said vapor phase isomerization is an EB dealkylation type, and toluene produced in the transalkylation section 58, as well as any stream of imported toluene (not shown). Thus, little or no toluene in the effluent from the transalkylation section 58 is recycled to the transalkylation section 58. In the preferred embodiment, benzene from benzene column 21 is sent to transalkylation section 58 (not shown in FIG. 1) in an amount that optimizes the methyl to ring ratio such that xylenes production in said unit is maximized. The benzene that is not processed in transalkylation section 58 can be recovered for sale or hydrogenation to produce cyclohexane or can be fed to the toluene methylation section 31 for additional xylenes production. The effluent from the transalkylation section 58 is supplied by line 60 to the stabilizer column 51.

Optionally, where orthoxylene production is desired, part or all of the bottoms stream from the xylene rerun column 44 can be fed via line 61 to orthoxylene column 62. Orthoxylene product is collected overhead via line 63, while the orthoxylene column bottoms heavies are sent to the heavy aromatics column 55 via line 64. If excessive orthoxylene is produced above production needs, a portion or all of the orthoxylene can be processed across either liquid phase isomerization section 42 or vapor phase isomerization section 48 or transalkylation section 58 to produce more paraxylene.

Figure 2:
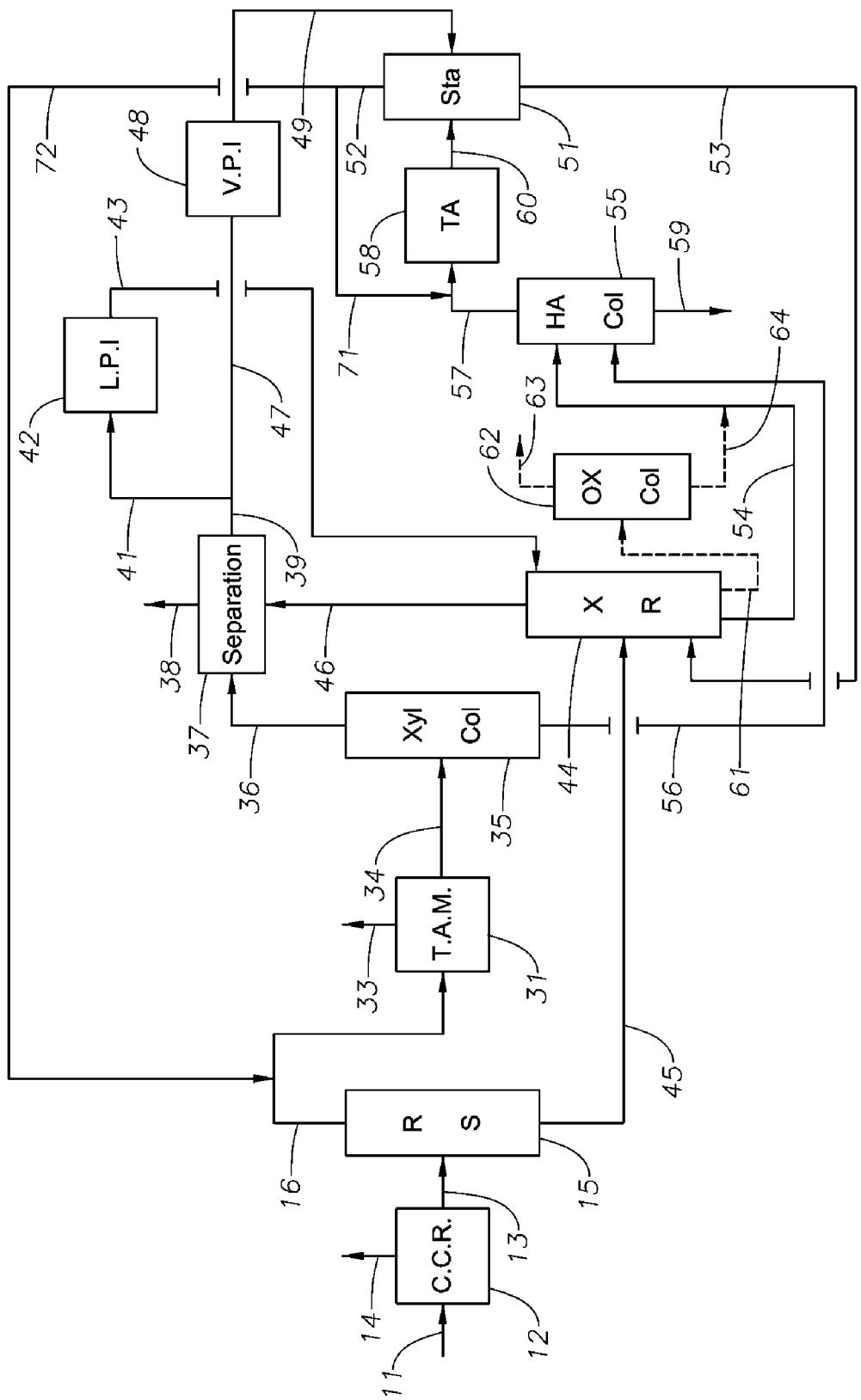
FIG. 2 is a flow diagram illustrating a process for producing para-xylene from catalytic reformate according to a modification of the first embodiment of the invention.

One modification of the process shown in FIG. 1 is illustrated in FIG. 2, in which like reference numerals are used to indicate like components to those shown in FIG. 1. In particular, in the process shown in FIG. 2, there is no provision for non-aromatics or benzene recovery and so the extraction section 17 and the benzene column 21 of FIG. 1 are omitted. Thus, in this modification, after the $C_{5-}$ fraction of the reformer effluent is removed in a depentanizer (not shown), the effluent is fed via line 13 to a reformate splitter section 15 which separates a $C_6/C_7$-containing overhead stream from a $C_{8+}$-containing bottoms stream. The $C_6/C_7$-containing overhead stream is fed via line 16 to the toluene methylation section 31, with no benzene extraction step, and, as in the FIG. 1 embodiment, the $C_{8+}$-containing bottoms stream is fed via line 45 to the xylene rerun column 44. Another noticeable change affects the stabilizer column 51 overhead liquid $C_6/C_7$ stream which is collected via line 52. This stream can either be recycled to the inlet of the transalkylation section 58 via line 71, or to the inlet of the toluene methylation section 31 via line 72, or any combination of both options. Factors impacting the decision to recycle a portion of stream 52 to transalkylation vs. toluene methylation include desired catalyst cycle length in the transalkylation section (which could be extended by the presence of lighter components such as $C_6/C_7$ in the feed to the transalkylation section) and the desired methyl/ring ratio in the transalkylation section 58.

Figure 3:
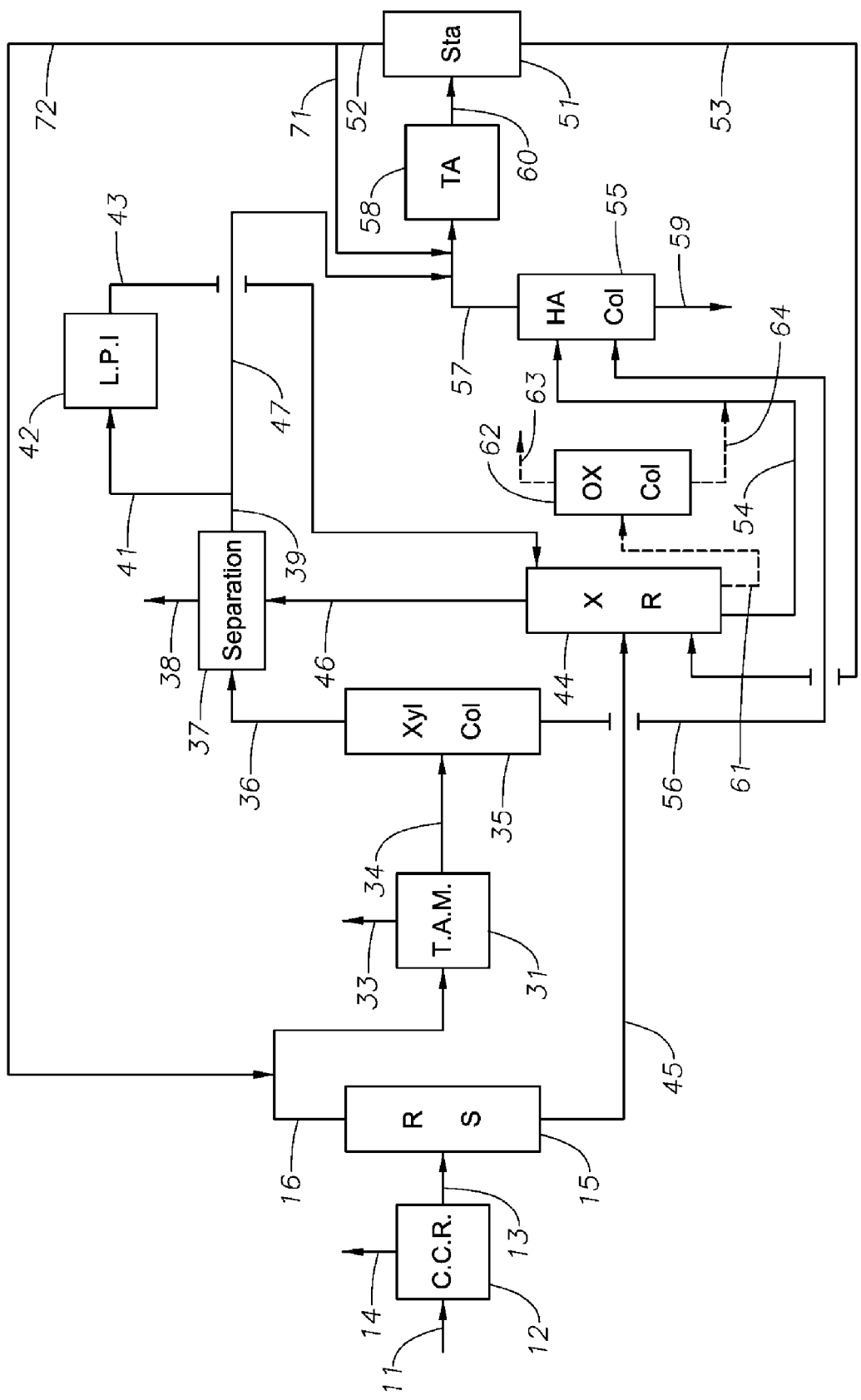
FIG. 3 is a flow diagram of a process for producing para-xylene from catalytic reformate according to a further modification of the first embodiment of the invention.

Another modification of the process shown in FIG. 1 is illustrated in FIG. 3, in which like reference numerals are again used to indicate like components to those shown in FIG. 1. In particular, in the process shown in FIG. 3, the vapor phase xylenes isomerization section 48 of FIG. 1 is omitted. Instead, the paraxylene depleted effluent of separation section 37 is collected via line 39 and can be fed in the liquid phase via line 41 to a liquid phase xylenes isomerization section 42 where xylenes are isomerized to equilibrium. Alternatively, the paraxylene depleted effluent of separation section 37, collected via line 39, is transferred via line 44 to transalkylation section 58, where remaining ethylbenzene will be converted to benzene and some xylenes isomerization will occur over the transalkylation catalyst system. Any combination of both options for the separation section 37 effluent, namely liquid phase isomerization or transalkylation, is acceptable. The decision to direct the separation section 37 effluent to one or the other process will depend on the ethylbenzene content in said separation section 37 effluent. Alternatively, a purge stream to or from the liquid phase isomerization section 42 can be processed across the toluene methylation section 31, or across an ethylbenzene isomerization unit (not shown), to control the ethylbenzene concentration. Although shown with the embodiment of FIG. 2 in which the extraction section 17 and the benzene column 21 of FIG. 1 are omitted, it will be appreciated that the process of FIG. 3 can be conducted with the extraction section 17 and the benzene column 21 of FIG. 1 present.

Figure 4:
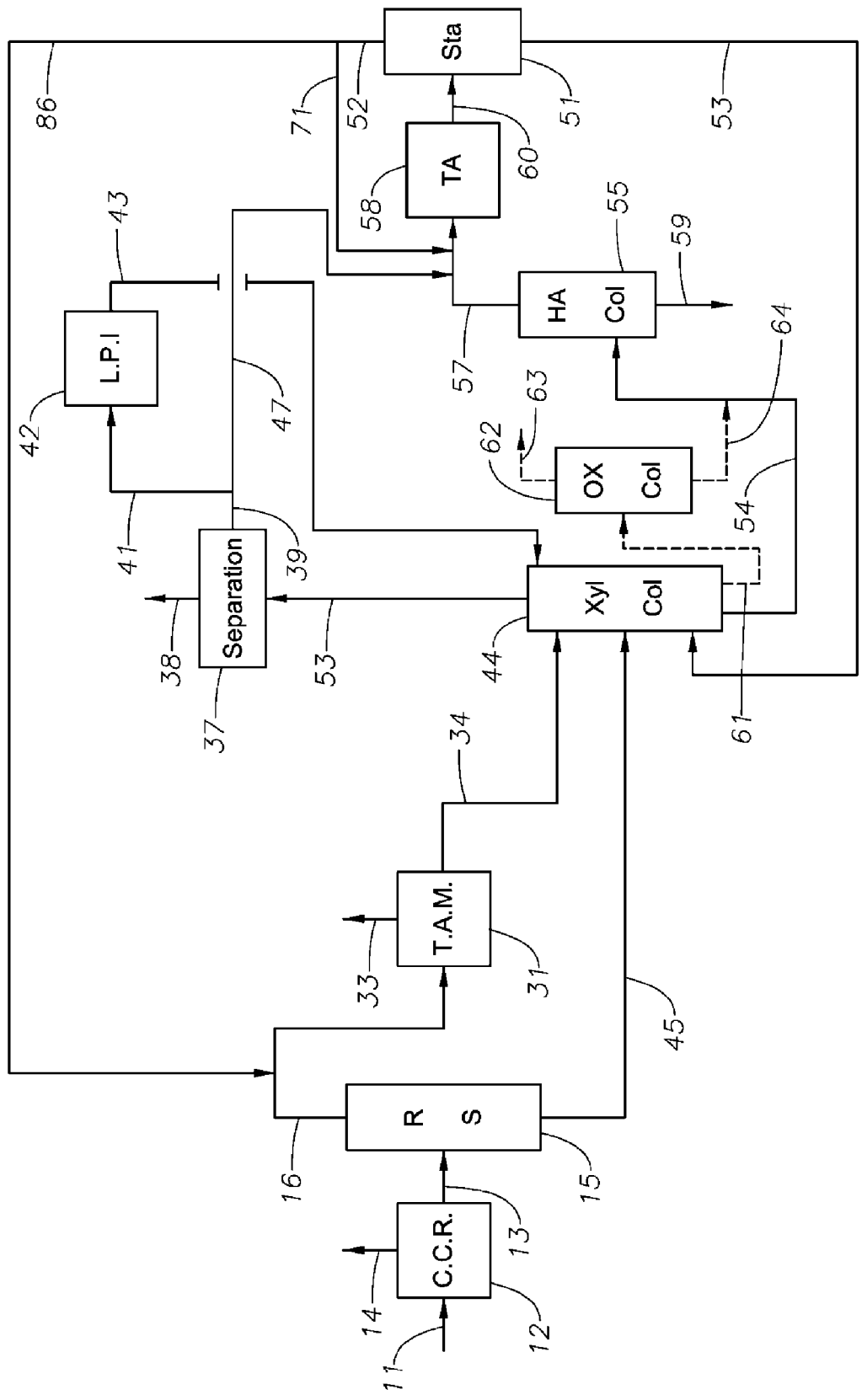
FIG. 4 is a flow diagram of a process for producing para-xylene from catalytic reformate according to a yet further modification of the first embodiment of the invention.

A further modification, applicable to each of the processes of FIGS. 1 to 3, is shown in FIG. 4 in which the xylene column 35 is combined with xylene rerun column 44 in a single column. In this embodiment, the toluene methylation section 31 effluent is now sent via line 34 to the larger xylene rerun column 44 together with the $C_{8+}$ bottoms stream from the stabilizer column 51 in line 53, the $C_{8+}$-containing bottoms stream 45 from the reformate splitter 15 and optionally, the effluent from the liquid phase isomerization section 42 in line 43.

In a modification (not shown) of any of the process shown in FIGS. 1-4, the product from the toluene methylation section 31 is fed to a separator drum which produces three separate phases including a liquid hydrocarbon stream, a liquid water and methanol stream, and an olefin containing offgas stream. The separation can be carried out in one or more drums with cooling between the drums consisting of air, cooling water, or some suitable coolant stream including refrigeration. The drums can either be horizontal or vertical, or a combination thereof. Horizontal drums may contain internal baffles. The horizontal drum may contain a water boot to collect the water phase. An internal demister pad may be employed to minimize liquid carryover with the off-gas. The vertical drum may also contain the same features as the horizontal drum, as one skilled in the art will be able to design. A combination of coolers can be also be used to cool the streams between the drums. The coolant exchangers may also be situated inside the separator drums. The separator drum(s) may also be combined with the quench tower to save capital.

The hydrocarbon stream may be further processed through a distillation section, such as a toluene distillation tower and/or xylenes distillation tower 35, to separate the hydrocarbons further. The water/methanol stream is fed to a methanol stripping column to remove hydrocarbons, methanol, and other oxygenated compounds from the water. The stream containing methanol, hydrocarbons and other oxygenated compounds may be recycled back to the toluene methylation section 31. The water stream may contain acids, such as formic acid, acetic acid or the like, which may reduce the pH of the stream. The water stream can be neutralized by treating with caustic, ammonia, sodium carbonate, or any other neutralizing agent known to one skilled in the art. The waste water stream can be treated at different locations; such as in the reactor effluent to the bottom of the methanol stripper, or any location between. The olefins containing stream is sent to further processing to remove contaminants before final recovery of the valuable olefin components.

In one embodiment, the toluene methylation section 31 comprises a reactor, regenerator for the catalyst, catalyst cooler, heat exchanger equipment, and gas/solids separation equipment. The reactor effluent may contain catalyst particulates, which can be separated from the reactor effluent stream using gas/solids separation equipment such as cyclones, centrifuges, gas filters, liquid filters, wash columns, or even, columns, tanks or settlers, or a combination thereof. This equipment may be located internal to the reactor vessel, for example, a cyclone or multiple cyclones, but is preferably external to the reactor vessel. The gas/solids equipment may be located either upstream of any heat exchange equipment used to recover heat from the reactor effluent stream or downstream of the heat exchange equipment. Such heat exchange equipment includes steam generators to produce steam with pressure ranging from 10 psig to 1200 psig, or heat exchange equipment to heat a process fluid using the enthalpy from the reactor effluent stream, or a combination thereof. Flue gas from the regenerator may also contain catalyst fines, which must be reduced for discharge into the atmosphere. These fines can be recovered from the flue gas using many different techniques, including cyclone or multiple cyclones, an Electrostatic Precipitator, a wash column, a centrifuge, or a combination thereof. The flue gas solids recovery equipment may be upstream or downstream of any process heat exchange equipment, such as a CO boiler or any other heat exchange equipment commonly used in flue gas services. The catalyst particulates recovered from the reactor effluent or the regenerator may be returned to the reaction zone, or the regenerator zone, or both, either directly or indirectly, for example, through an intermediate storage vessel, or discharged from the system.

Catalyst may be withdrawn from the regenerator and fed to a heat exchange device, also known as a catalyst cooler, in order to remove the heat generated in the regenerator by the combustion of coke and other hydrocarbons on the catalyst. The withdrawal of the catalyst from the regenerator may be on a continuous or intermittent basis and of varying rates. The cooled catalyst is then fed back to the regenerator. By controlling the flow of catalyst through the catalyst cooler, and/or the amount of heat removed, the temperature of the catalyst bed in the regenerator is controlled. Depending on the amount of coke to be burned in the regenerator, the catalyst cooler may operate between maximum rates and complete shutdown. The flow of catalyst withdrawal from the regenerator is controlled using a slide valve or other suitable valve for controlling the flow of solids including solids fluidized by a suitable vapor stream (aeration media) injected into the piping both in and out of the catalyst cooler. The aeration media may be air, steam, nitrogen, hydrocarbon, and/or other suitable gas which may also be injected into the catalyst cooler to ensure fluidization of the solids within the catalyst cooler, and control the heat transfer coefficient from the fluidized catalyst, thus ensuring adequate heat transfer of the hot catalyst to the cooling medium. The catalyst cooler may also be used to preheat boiler feed water, generate steam of different pressures, preheat and/or vaporize a process stream, or heat air. The catalyst cooler is typically attached to the regenerator, attached to a separate structure for support, or enclosed completely or partially (stab in) inside the regenerator vessel.

The invention will now be more particularly described with reference to the following non-limiting Example.

Example 1

This simulated example illustrates how the addition of a toluene alkylation with methanol unit increases the para-xylene output of an aromatics complex based on the same feedstock as a conventional aromatics complex where xylenes are generated in the reforming and transalkylation sections. In this example, it is assumed that all xylenes will be converted to para-xylene (no ortho-xylene production). The results are shown in Table 1 below.

TABLE 1

| | BPD 29000 kta 1245.3 | | | | | | | |
|---|---|---|---|---|---|---|---|---|
| | CCR | | Xylenes_Recovery (only) | | Xylenes_Recovery and Transalkylation | | Xylenes_Recovery with TAM and Transalkylation | |
| | Reformate | | Percent | KTA | Percent | KTA | Percent | KTA |
| H2 | 4.0 | 49.8 | 3.7 | 46.4 | 3.0 | 37.6 | 3.0 | 41.3 |
| C1 | 1.3 | 16.2 | 0 | 0.0 | 0.0 | 0.0 | 0.0 | 0.0 |
| C2 | 2.1 | 26.2 | 0 | 0.0 | 0.0 | 0.0 | 0.0 | 0.0 |
| Fuel | | 0.0 | 5.0 | 62.5 | 10.0 | 127.9 | 11.2 | 139.6 |
| C3 | 2.8 | 34.9 | 0 | 0.0 | 0.0 | 0.0 | 0.0 | 0.0 |
| C4 | 3.5 | 43.6 | 0 | 0.0 | 0.0 | 0.0 | 0.0 | 0.0 |
| LPG | | 0.0 | 6.3 | 78.5 | 6.3 | 78.5 | 6.3 | 78.5 |
| C5 | 2.9 | 36.1 | 0 | 0.0 | 0.0 | 0.0 | 0.0 | 0.0 |
| C6 | 4.4 | 54.8 | 0 | 0.0 | 0.0 | 0.0 | 0.0 | 0.0 |
| C7 | 3.5 | 43.6 | 0 | 0.0 | 0.0 | 0.0 | 0.0 | 0.0 |
| C8 | 0.9 | 11.2 | 0 | 0.0 | 0.0 | 0.0 | 0.0 | 0.0 |
| Raffinate | | 0.0 | 11.7 | 145.7 | 11.7 | 145.7 | 11.7 | 145.7 |
| Bz | 3.5 | 43.6 | 6.7 | 83.6 | 15.7 | 195.7 | 10.9 | 135.2 |
| Tol | 18.0 | 224.2 | 0 | 0.0 | 0.0 | 0.0 | 0.0 | 0.0 |
| Xyl | 24.0 | 298.9 | 0 | 0.0 | 0.0 | 0.0 | 0.0 | 0.0 |
| EB | 4.8 | 59.8 | 0 | 0.0 | 0.0 | 0.0 | 0.0 | 0.0 |
| Px | | 0.0 | 23.0 | 286.9 | 45.0 | 560.9 | 51.8 | 645.1 |
| A$_9$ | 18.0 | 224.2 | 0 | 0.0 | 0.0 | 0.0 | 0.0 | 0.0 |
| A$_{9/10}$+ | 4.9 | 61.0 | 0 | 0.0 | 0.0 | 0.0 | 0.0 | 0.0 |
| A$_{11}$+ (FO) | 1.4 | 17.4 | 1.4 | 17.4 | 1.4 | 17.4 | 3.0 | 37.3 |
| Mogas | | 0.0 | 42.1 | 524.3 | 6.8 | 84.9 | 6.1 | 76.0 |

TABLE 1-continued

| BPD 29000 kta 1245.3 | | | | | | | |
|---|---|---|---|---|---|---|---|
| | CCR | Xylenes_Recovery (only) | | Xylenes_Recovery and Transalkylation | | Xylenes_Recovery with TAM and Transalkylation | |
| | Reformate | Percent | KTA | Percent | KTA | Percent | KTA |
| MeOH | 0 | 0.0 | 0.0 | 0.0 | 0.0 | −9.4 | −116.9 |
| Water | | | | | | 5.1 | 63.6 |

In Table 1, each aromatics complex employs the same feedstock (1245.3 kTa naphthas) qualitatively and quantitatively. Furthermore the reforming section provides the same product slate in all cases, the product slate being listed in column #1 entitled "CCR Reformate". Column #2 entitled "Xylenes Recovery (only)" shows para-xylene production if only reformer xylenes are recovered (no transalkylation unit). Column #3 entitled "Xylenes Recovery and Transalkylation" shows para-xylene production in a conventional aromatics complex, where a transalkylation unit has been added to produce additional xylenes. Column #4 entitled "Xylenes Recovery with TAM and Transalkylation" shows para-xylene production from an aromatics complex where a toluene alkylation with methanol unit has been added to a conventional aromatics complex with a transalkylation unit.

As can be seen from Table 1, on the same feedstock and reforming section output basis, para-xylene production for a conventional aromatics complex is 560.9 kTa while para-xylene production for a conventional complex where toluene alkylation with methanol unit has been added is 645.1 kTa.

Furthermore, para-xylene production is often favored over benzene production due to higher margins. Benzene can be fed to the transalkylation section for additional xylenes production, but this production is limited by methyl to ring ratio. However when a toluene methylation section is available, all benzene can be converted to xylenes—and further to para-xylene—if desired. Hence in the case of column #4, an additional 135.2 kTa of benzene is available for further para-xylene production. In this case, the amount of the complex paraxylene can be increased to ~829 kta, an increase of nearly 50% para-xylene production over the complex without toluene methylation.

Thus, the combination of a toluene alkylation with methanol unit and transalkylation unit in an aromatics complex provides significantly higher para-xylene production than a conventional aromatics complex with the same feedstock and reforming section output. Conversely, to achieve similar para-xylene production as a conventional aromatics complex using the combination of a toluene alkylation with methanol unit and transalkylation unit requires less feed, allowing for a smaller refinery section upstream. In other words, the combination of a toluene alkylation with methanol unit and transalkylation unit in an aromatics complex allows for similar para-xylene production as a conventional aromatics complex using less crude oil.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. Apparatus for producing para-xylene, the apparatus comprising:
   (a) a catalytic reformer for producing a reformate stream comprising $C_{6+}$ aromatic hydrocarbons;
   (b) a first separation system for separating the reformate stream into at least a toluene-containing stream, a $C_8$ aromatic hydrocarbon-containing stream and a $C_{9+}$ aromatic hydrocarbon-containing stream;
   (c) a toluene methylation unit for converting toluene in the toluene-containing stream to xylenes and produce a methylated effluent stream;
   (d) a transalkylation unit for converting $C_{9+}$ aromatics in the $C_{9+}$ aromatic hydrocarbon-containing stream to $C_{8-}$ aromatics and produce a transalkylation effluent stream;
   (e) a second separation system for recovering para-xylene from the $C_8$ aromatic hydrocarbon-containing stream, the methylated effluent stream and the transalkylation effluent stream to produce at least one para-xylene depleted stream;
   (f) a liquid phase xylene isomerization unit for isomerizing xylenes in the at least one para-xylene depleted stream to produce a first isomerized stream;
   (g) a first recycle system for recycling at least part of the first isomerized stream to the second separation system; and
   (h) a second recycle system for recycling at least part of the transalkylation effluent stream to the toluene methylation unit and second separation system.

2. The apparatus of claim 1 and further comprising:
   (i) a vapor phase xylene isomerization unit for isomerizing xylenes in the at least one para-xylene depleted stream to produce a second isomerized stream; and
   (j) a third recycle system for recycling at least part of the second isomerized stream to the second separation system.

3. The apparatus of claim 1 and further comprising:
   (k) a third separation system for recovering ortho-xylene from one or more of the $C_8$ aromatic hydrocarbon-containing stream, the methylated effluent stream and a transalkylation effluent stream.

4. The apparatus of claim 1 and further comprising:
   (l) an extraction system between the first separation system and toluene methylation unit for removing non-aromatics from the toluene-containing stream and produce a toluene-containing aromatic stream; and
   (m) a fourth separation system for separating the toluene-containing aromatic stream into a benzene stream and a toluene stream, wherein the toluene stream is supplied to the toluene methylation unit.

5. The apparatus of claim 1 and further comprising:
   (n) a fifth separation system for recovering unconverted toluene from the methylated effluent stream; and (o) a fourth recycle system for recycling at least part of the unconverted toluene to the toluene methylation unit.

6. The apparatus of claim 1 wherein the first separation system comprises a dividing wall column.

7. The apparatus of claim 1 wherein second separation system comprises an adsorption process.

8. The apparatus of claim 1 wherein second separation system comprises a crystallization process.

* * * * *